United States Patent [19]
Chatterjee et al.

[11] Patent Number: 5,925,355
[45] Date of Patent: Jul. 20, 1999

[54] PREPARATIONS OF CRATAEGUS SPECIES, PHARMACEUTICAL COMPOSITIONS AND THEIR USE FOR PREVENTING SUDDEN DEATH DUE TO CARDIAC ARREST AND REPERFUSION-CAUSED CARDIOVASCULAR LESIONS

[75] Inventors: Shyam Sunder Chatterjee; Hermann Ernst Jaggy, both of Karlsruhe, Germany

[73] Assignee: Willmar Schwabe GmbH & Co., Germany

[21] Appl. No.: 08/592,333

[22] PCT Filed: Jul. 28, 1994

[86] PCT No.: PCT/EP94/02497

§ 371 Date: Jan. 29, 1996

§ 102(e) Date: Jan. 29, 1996

[87] PCT Pub. No.: WO95/03816

PCT Pub. Date: Feb. 9, 1995

[30] Foreign Application Priority Data

Jul. 29, 1993 [DE] Germany .............................. 43 25 532

[51] Int. Cl.⁶ ..................................................... A61K 35/78
[52] U.S. Cl. ............................................................ 424/195.1
[58] Field of Search ........................................... 424/195.1

[56] References Cited

U.S. PATENT DOCUMENTS 2,799,618  7/1957  Bersin et al. .............................. 514/25
5,064,675  11/1991  Jensen et al. ........................... 426/597

FOREIGN PATENT DOCUMENTS 1064294    7/1992  China ............................. A61K 31/70
A 2 315 946  1/1977  France ........................... A61K 35/78
A 11 03 519  3/1961  Germany .

OTHER PUBLICATIONS

Li et al., J Tradit Chin Med 4(4): 289–292 (1984) (Abstract).
Li et al., J Tradit Chin Med 4(4): 283–288 (1984) (Abstract).
Fang et al., Zhongcaoyao 16(12): 548–51 (1985) (Abstract).

*Primary Examiner*—Jean C. Witz
*Attorney, Agent, or Firm*—McDonnell Boehnen Hulbert & Berghoff

[57] ABSTRACT

The preparation of a total extract of leaves and flowers of appropriate Crataegus species is described as well as three new fractions of said total extract and their use as pharmaceutical compositions for preventing sudden death due the cardiac arrest and reperfusion-caused cardiovascular lesions and other reperfusion-caused life-threatening pathological conditions.

14 Claims, 1 Drawing Sheet

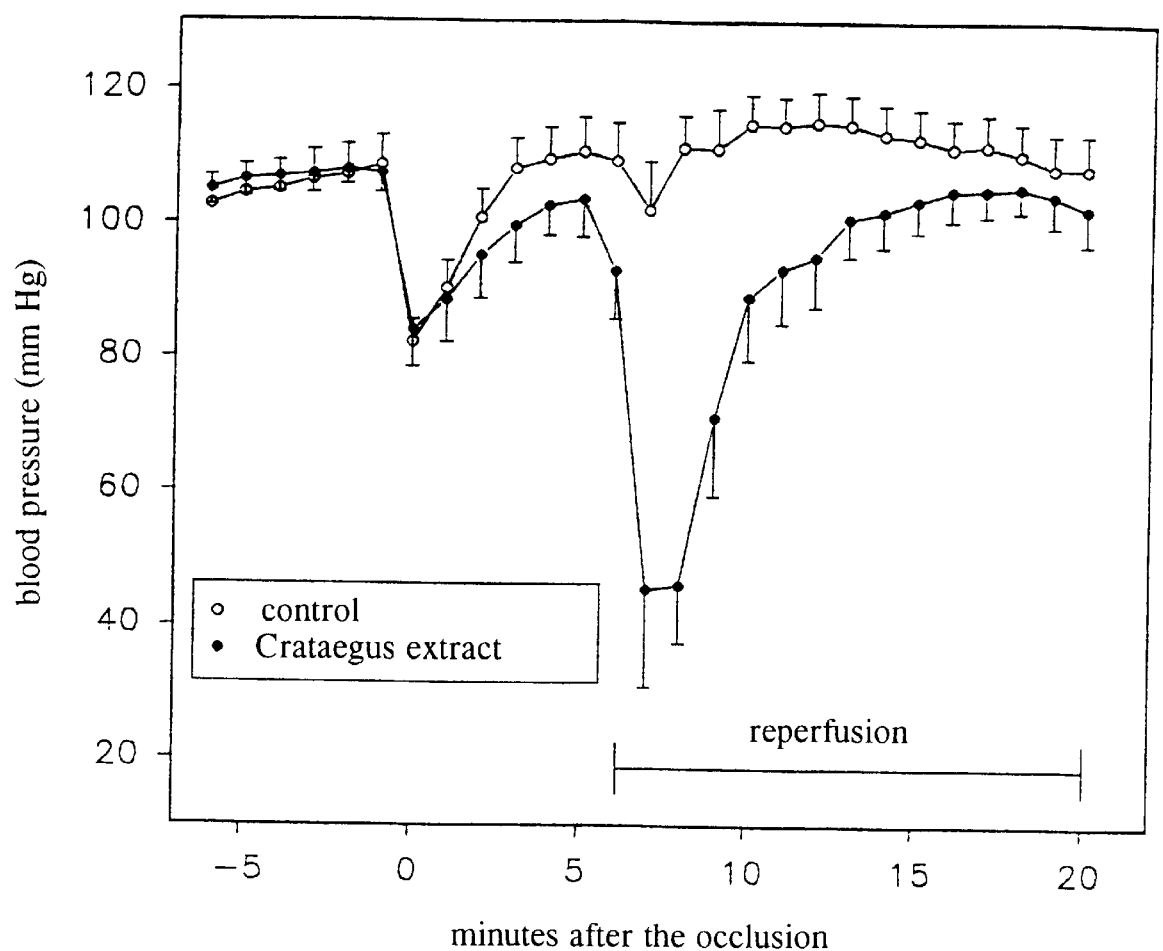

PREPARATIONS OF CRATAEGUS SPECIES, PHARMACEUTICAL COMPOSITIONS AND THEIR USE FOR PREVENTING SUDDEN DEATH DUE TO CARDIAC ARREST AND REPERFUSION-CAUSED CARDIOVASCULAR LESIONS

Numerous clinical studies demonstrate that extracts from the leaves and flowers and/or fruits of Crataegus species are beneficial for the treatment of patients with decreasing cardiac performance. Therapeutic experience over many years also demonstrated the therapeutic efficacy of such extracts in case of unstable functional-vegetative stenocardias as well as in case of mild forms of bradycardic arrhythmia. These findings led Commission E of the German Health Authorities [Kommission E beim deutschen Bundesgesundheitsamt] to publish a monograph (see Official Federal Gazette [Bundesanzeiger] dated Mar. 1, 1984) with the following indications:

Decreasing cardiac performance corresponding to stages I to II according to NYHA; sensation of pressure and constriction in the cardiac region; senile heart not yet requiring digitalis therapy and mild forms of bradycardic arrhythmia.

Up to the present, the known therapeutic benefit as well as the pharmacodynamic spectrum of action of these Crataegus extracts are in general explained by the presence of flavonoids and oligomeric procyanidins in the Crataegus extracts. The pharmaceutical preparations are therefore standardized to these components. One of these known Crataegus extracts (WS 1442) contains approximately 18.5 to 19.5% oligomeric procyanidins.

The invention is based on unexpected findings obtained in animal tests using rats with experimentally induced ischemia. According to these findings, an extract from leaves with flowers of appropriate Crataegus species such as *Crataegus monogyna* JAQUIN emend. LINDMAN, *Crataegus laevigata* (POIRET) DE CANDOLLE syn. *Crataegus oxyacantha* L. p. p. et duct., *Crataegus azarolus* L., *Crataegus nigra* WALDSTEIN et KITAIBEL and *Crataegus pentagyna* WALDSTEIN et KITAIBEL ex WILLDENOW, obtained by extraction with a mixture of water and a water-miscible organic solvent such as ethanol a) has cardioprotective effects in case of cardiac ischemia and life-threatening reperfusion-induced cardiovascular lesions
  b) and the active substances of the Crataegus extract known up to the present are not responsible for these effects.

These effects of the Crataegus extract—in the following also called fraction (a)—allow to deduce a therapeutic application of Crataegus extracts in the prevention and treatment of short periods of cardiac ischemia (circulatory disturbances of the heart), reperfusion-caused cardiac lesions and sudden death due to cardiac arrest as well as other life-threatening reperfusion-caused pathological conditions.

Extended tests with three new fractions of this Crataegus extract indicate that the particularly active component of the Crataegus extract has a molecular weight of more than 3000 Dalton. The structure of this component is not yet known.

Description of the tests

Substances tested

Fraction (a) Total extract from leaves with flowers of *Crataegus monogyna, laevigata, azarolus, nigra* and *pentagyna,* obtained by extraction with ethanol 45% by weight at 60° C. with a content of 18.5 to 19.5% oligomeric procyanidins;

Fraction (b) Fraction of the compounds with molecular weights of more than 3000 Dalton, obtained by means of ultrafiltration of fraction (a) using a membrane filter with a cut-off limit of 3000 Dalton;

Fraction (c) obtained by means of liquid—liquid distribution (countercurrent extraction) of fraction (a) in butanol/water;

Fraction (d) obtained from fraction (a) from which the flavonoids and proanthocyanidins have been removed through adsorption using an adsorbent which binds these compounds, in particular hydroxypropylated polydextran, polyamides, aluminium oxide or activated charcoal.

Test method

We used the method described by Selye [H. Selye et al., Angiology 11 (1960), 398–407] applied in male Sprague-Dawley rats with a body weight between 250 and 350 g and anaesthetised with pentobarbital. Cardiac ischemia was provoked by ligature of the coronary artery and reperfusion initiated by reopening the ligature after a 7-minute ischemia. Blood pressure and heart rate of the animals were measured prior to and during the ischemia as well as after the reperfusion; we also determined the duration and type of cardiac arrhythmia during the reperfusion phase. Under such test conditions, approximately 50% of the control animals die within a reperfusion period of 15 minutes. Causes for such mortalities are the hypotensive crisis and ventricular fibrillation induced by and occurring immediately after reperfusion. This pharmacological model is therefore appropriate for testing the efficacy of pharmaceutical substances which may prevent or have beneficial effects on sudden death due to cardiac arrest or reperfusion-caused cardiovascular lesions.

Test results

In this model, the total Crataegus extract, i.e. fraction (a), and fractions (b), (c) and (d) were investigated. In a first test series, the total extract was administered orally by means of a pharyngeal probe at a dose of 100 mg/kg/day over a period of 6 days. On the 7th day, the animals received an oral dose of 50 mg/kg and were then subjected to the test one hour later.

Test results of the animals treated with the total extract and of the control animals treated only with solvent are summarized in Table I and Figure I. FIG. I shows the mean blood pressure (mm Hg±standard deviation) of the surviving animals in the control group (n=8) and the Crataegus extract-treated group (n=16). These test results show that the administration of total Crataegus extract protects the animals against arrhythmia induced by short-time ischemia and reperfusion, against lifethreatening hypotensive crisis and possible death.

TABLE I

| Group | Fibrillation | | Tachycardia | | Mortality (%) |
|---|---|---|---|---|---|
| | frequency (%) | duration (sec.) | frequency (%) | duration (sec.) | |
| Control | 100 | 27.8 + 5.37 | 100 | 47.1 + 6.74 | 50 |
| Fraction (a) | 0 | 0 | 62 | 20.0 + 4.56 | 0 |

In further test series, fraction (a) was investigated at different doses and according to different treatment plans. Test results are summarized in Table II.

TABLE II

| Dose (mg/kg) | Treatment plan | Protection against | | |
|---|---|---|---|---|
| | | mortality | arrhythmia | hypotensive crisis |
| 100 | daily for 6 days + 50 mg/kg 1 h before test | +++ | +++ | +++ |
| 100 | 1 day before + 50 mg/kg 1 h before test | ++ | +++ | − |
| 100 | 1 day before + 100 mg/kg 1 h before test | +++ | +++ | + |
| 100 | 1 h before test | + | ++ | − |
| 50 | 1 h before test | + | + | − |
| 25 | 1 h before test | − | − | − |
| 100 | 4 h before test | + | ++ | − |
| 100 | 8 h before test | − | + | − |

These test results show that the maximum effects of fraction (a) against cardiac ischemia and reperfusion-induced lesions may only be obtained after long-term administration of fraction (a) and that a mere short-lasting but reliable protective effect can be expected after administration of 2×100 mg/kg of fraction (a) (1 day+1 hour before the ischemia).

In further tests in which fraction (a) was applied intravenously at different doses 15 minutes prior to the test beginning, no definitive effects of fraction (a) could be ascertained.

The fractions described were then tested in a similar way using adequate doses according to the respective yields related to the total extract.

TABLE III

Comparison of the effects of the total extract and the effects of various fractions

| Fraction (Dose) | Protection against | | |
|---|---|---|---|
| | mortality | arrhythmia | hypotensive crisis |
| Fraction (a) (100 mg/kg) | +++ | +++ | + |
| Fraction (b), components with a molecular weight >3000 Dalton from ultrafiltration (20 mg/kg) | +++ | +++ | ++ |
| Fraction (c) with a molecular weight <3000 Dalton from filtrate of ultrafiltration (80 mg/kg) | ++ | + | − |
| Fraction (d) without flavonoids and proanthocyandins (50 mg/kg) | +++ | +++ | ++ |

A comparison of the effects of the fractions in table III clearly shows that the best effects are to be found in those fractions of the extract which contain substances with higher molecular weight and that the presence of flavonoids or oligomeric procyanidins which, till now, had been considered as the effective components of Crataegus extracts, are not necessary.

Preferred pharmaceutical compositions of the present invention for the prophylaxis and therapy of reperfusion-caused cardiovascular lesions, for the prevention of sudden death due to cardiac arrest as well as other life-threatening reperfusion-caused pathological conditions therefore contain a sufficient amount of non-flavonoid polymeric compounds of Crataegus fractions with a high content of these active substances.

In accordance with the present invention, they can be manufactured as described below:

a) Extraction of the comminuted plant material with mixtures of water, acetone, C1–C4 alkanols or mixtures of water and the water-miscible organic solvents mentioned, preferably ethanol 45% by weight (fraction (a));

b) Separation of low-molecular weight compounds from fraction (a) by ultrafiltration through an appropriate membrane filter with a cut-off limit of 3000 Dalton (fraction (b));

c) Obtained by liquid—liquid distribution of fraction (a) in butanol/water (fraction (c));

d) Gel filtration of fraction (a) with polydextrans or other gels appropriate for separation using the molecular sieve effect, for the separation of flavonoids and proanthocyanidins and other low-molecular compounds (fraction (d)).

For the prophylaxis and therapy of reperfusion-caused cardiovascular lesions and for the prevention of sudden death due to cardiac arrest, fraction (a), (b), (c) and (d), preferably fraction (b), can be used in all pharmaceutical forms for oral administration, such as coated tablets, tablets, capsules, solutions. For the manufacturing of such pharmaceutical preparations, the fractions can be formulated in the usual manner using carriers such as lactose, starch, microcrystalline cellulose, magnesium stearate and talc or water, alcohols, polyethylene glycols, glycerol ester. Preservative agents, lubricants, wetting agents, emulsifyers, coloring agents, flavor correctives and flavoring agents can be used as additives.

The daily doses administered are 50 to 500 mg of total Crataegus extract (fraction (a)); in case of pharmaceutical preparations with enriched active-substance fractions (fractions (b), (c) and (d)) the dose may be decreased accordingly.

The examples illustrate the preferred procedures for the preparation of the fractions.

EXAMPLE 1

100 kg of dry leaves and flowers of Crataegus species (commercial mixture of about 77% *Crataegus monogyna*, about 2% *C. laevigata*, about 4% *C. azarolus*, about 16% *C. nigra* and about 1% *C. pentagyna*) are comminuted by milling and subjected to vortex extraction with a Dispax Generator® with 1000 kg 45 weight percent aqueous ethanol for 1 hour at 60° C. The extract is separated by continuous centrifugation. The plant material is once more extracted in the same manner with 1000 kg of 45 weight percent of aqueous ethanol for 1 hour at 60° C. The combined extract solutions are concentrated at a pressure of about 400 mbar and 80° C.; the concentrated extract is dried in a vacuum shelf dryer at 60° C. and 5–10 mbar.

Yield for total extract (fraction (a))

20% calculated for dry Crataegus leaves with flowers. The extract contains about 18.75% of oligomeric procyanidins.

EXAMPLE 2

200 g of leaves with flowers of Crataegus species (mixture of about 63% *C. monogyna*, about 3% *C. laevigata*, about 9% *C. azarolus* and about 25% *C. nigra/pentagyna*) are comminuted by milling and extracted with 2 liter of 40 weight percent acetone for 1 hour under stirring and in a reflux system. After separation of the extract solution, the residue is once more extracted with 2 liter of 40 weight percent aqueous acetone for 30 minutes under stirring and in a reflux system. The combined extract solutions are concentrated to dryness at 60° C. bath temperature and a pressure of 520–20 mbar.

Yield: 65.6 g of dry extract fraction (a), corresponding to 32.8% calculated for dry Crataegus leaves with flowers.

EXAMPLE 3

20 g of the extract from Crataegus leaves with flowers prepared with 40 weight percent aqueous acetone according to example 2 are added to 400 ml of water at 70° C. under stirring. After addition of 10 g of activated carbon the mixture is stirred for 1 hour. The activated carbon and undissolved components of the extract are filtered over a filtering layer. The filtrate is concentrated to dryness at 60° C. bath temperature and a pressure of 80–20 mbar.

Yield: 8.8 g of substance fraction (a), corresponding to 44% calculated for Crataegus extract.

EXAMPLE 4

85 kg of dry leaves with flowers of Crataegus species (mixture of about 76% C. monogyna, about 5% C. laevigata and about 19% C. nigra) are comminuted by milling and heated to 60° C. for 3 hours with 600 kg of methanol in a circulation extractor; thereafter the extract solution is separated. Thereafter the extract solution is concentrated at 60° C. and a pressure of 200–260 mbar, and dried in a vacuum shelf dryer at 60° C. and a pressure of 20 mbar.

Yield: 12.75 kg of dry extract fraction (a), corresponding to 15% calculated for dry Crataegus leaves with flowers.

EXAMPLE 5

200 g of leaves with flowers of Crataegus species (mixture of about 63% C. monogyna, about 3% C. laevigata, about 9% C. azarolus and about 25% C. nigra/pentagyna) are comminuted by milling and poured with 2 liter of boiling demineralized water and extracted for 15 minutes in a dispersing apparatus with blades. The extract solution is filtered off by filtration over a filtering layer on a cellulose basis. The plant residue is once more vortex extracted with 2 liter of boiling demineralized water for 15 minutes. The extract solution from the second extraction is also filtered over a filter bed on a cellulose basis. The extract solutions are combined and concentrated to dryness in a rotary evaporator at 60° C. bath temperature and a pressure of 50 mbar.

Yield: 52 g of fraction (a), corresponding to 26% calculated for dry Crataegus leaves and flowers.

EXAMPLE 6

20 g of extract from Crataegus leaves with flowers according to example 1 are added to 50 ml of 45 volume percent ethanol under stirring and fed to a column containing 200 g of cross-linked polyvinylpyrrolidone suspended in 45 volume percent ethanol. The flow rate is adjusted to 40 ml per 8 minutes. By means of a fraction collector, fractions of 40 ml respectively are collected. The first fractions containing substance are combined and concentrated to dryness in a rotary evaporator at 60° C. bath temperature and a pressure of 120–50 mbar.

Yield: 8.9 g of active component concentrate (free from flavonoid compounds and procyanidins), corresponding to 44.5 % calculated for extract.

EXAMPLE 7

6.65 g of the extract from Crataegus leaves with flowers prepared with 40 weight percent aqueous acetone according to example 2 are dispersed in 20 ml of demineralized water under heating to 50° C. and treatment with ultrasound. The hereby obtained solution is fed onto a gel bed from 100 g hydrophilic cross linked Dextran (Sephadex G-25 medium®) in water (height 57 cm, diameter 2.8 cm). The first 240 ml of column eluate containing substance are combined and concentrated to dryness in a rotary evaporator at 60° C. bath temperature and 50 mbar pressure.

Yield: 0.13 g residue (free from flavonoid compounds and procyanidins), corresponding to 1.95% calculated for extract.

EXAMPLE 8

80 g of total extract prepared according to example 1 are stirred for 15 minutes at 40° C. with 1.2 liter of 50 volume percent ethanol. The undissolved components of the extract are centrifuged, the supernatant liquid is filtered through a glass frit D3. The solution is ultrafiltered at a pressure of 2.5 bar through a spiral-wound regenerated cellulose-based ultrafiltration cartridge (Amicon® spiral-wound ultrafiltration cartridge type S1Y3) with a cut-off limit of 3000 Dalton.

The retained solution is concentrated to 400 ml and subsequently washed four times with 700 ml of 50 volume percent ethanol. The hereby obtained 200 ml of retained solution are removed, and the filter cartridge is rinsed with 1 liter of 70 volume percent ethanol. The retained solution and the rinsing liquid are concentrated to about 200 ml in a rotary evaporator at 60° C. and 40 mbar, whereby the ethanol is distilled off. The concentrate is deep frozen in an ethanol/dry ice bath at −40° C. and lyophilised under 0.22 mbar.

Yield: 15.35 g fraction (b), corresponding to 19.19% calculated for total extract.

EXAMPLE 9 a) 100 g of total extract prepared according to example 1 are dissolved in 1 liter of demineralized water with heating to 50° C. After cooling to room temperature the aqueous solution is extracted five times with 400 ml of water-saturated n-butanol in each case. The water phase is stored and further processed in step b).

The butanol phases are combined. Thereafter the obtained butanol solution is washed once with 500 ml of demineralized water. The aqueous solution is stored and further processed in step b).

The butanol solution is concentrated in vacuum at 60° C./30 mbar, whereby the n-butanol is distilled off by the addition of water. The residue is dried in vacuum at 60° C./17 mbar. Final weight of n-butanol fraction: 29.5 g.

b) The water phase obtained in step a) as well as the water solution obtained by rewashing of the butanol solution is concentrated under vacuum at 60° C./55 mbar and reduced via evaporation at 17 mbar. Final drying at 60° C./20 mbar in a vacuum shelf drier yields 71.4 g fraction (c) as residue from the water phase, corresponding to 71.4% calculated for total extract. By means of thin layer chromatography in the solvent system described in example 10 it is possible to detect chlorophyll, the flavonoid compounds and part of the oligomeric procyanidins in the n-butanol fraction. The water fraction (fraction (c)) contains procyanidins and as yet unknown active compounds.

EXAMPLE 10

50 g of total extract from Crataegus leaves with flowers are stirred with 200 ml demineralized water at 50° C. The suspension containing undissolved components is fed onto a gel bed from 1 kg Sephadex-LH 20® (hydroxypropylated cross-linked polydextran), 5suspended in water, in a glass column with 7.4 cm diameter and 100 cm filling height. The column is eluted with 5 liter of demineralized water. The eluates are examined for absence of the typical flavone glycosides of Crataegus of the Apigenin-type (Vitexin, Vitexin-2"-O-rhamnoside etc.) and flavonol glycosides of Quercetin (Hyperoside=Quercetin-3-O-galactoside, Rutin= Quercetin-3-O-rutinoside etc.) by means of thin layer chromatography on silica gel plates in the solvent ethyl acetate/ formic acid/acetic acid/water 100+11+11+27 parts by volume. The fractions after 1 liter pre-eluate up to 5 liter eluate are combined and concentrated to dryness in a rotary evaporator at 60° C./20 mbar.

Yield: 25.36 g of fraction (d), corresponding to 50.72% calculated for total extract.

EXAMPLE 11

Tablets with 50 mg of total Crataegus extract, fraction (a)

| | |
|---|---|
| 50 g | fraction (a) |
| 50 g | colloidal silicic acid (Aerosil ®) |
| 100 g | lactose |
| 25 g | microcrystalline cellulose |
| 24 g | corn starch |
| 1 g | magnesium stearate |

The first five ingredients are mixed, granulated and compressed after the addition of magnesium stearate in a tablet compressing machine to produce tablets of 250 mg.

EXAMPLE 12

Capsules with 50 mg of extract from Crataegus, fraction (b)

| | |
|---|---|
| 30 g | fraction (b) |
| 120 g | lactose |
| 50 g | colloidal silicic acid |

The ingredients are mixed homogeneously and processed in the usual manner to produce capsules with a filling weight of 200 mg.

EXAMPLE 13

Coated Tablets

| | |
|---|---|
| fraction (d) | 40.00 mg |
| microcrystalline cellulose | 100.00 mg |
| lactose | 60.00 mg |
| colloidal silicic acid | 50.00 mg |
| talc (in tablet core) | 4.50 mg |
| magnesium stearate | 0.50 mg |
| hydroxypropylmethylcellulose | 12.00 mg |
| talc (in coating) | 0.50 mg |
| weight of a coated tablet | app 267.50 mg |

EXAMPLE 14

Solution

| | |
|---|---|
| 40 g | fraction (c) |
| 10 g | flavoring essence |
| 5 g | sodium saccharinate |
| 460 g | ethanol |
| 475 g | purified water |

We claim:

1. A composition obtained from Crataegus species flowers and leaves prepared by a process comprising (a) extracting Crataegus species leaves and flowers with 45 weight percent ethanol at 60° C.; and (b) ultrafiltering the resulting extract through a membrane filter with a cut-off limit of 3000 Dalton to yield an ultrafiltered extract consisting of components having a molecular weight of at least about 3000.

2. A composition obtained from Crataegus species flowers and leaves prepared by a process comprising (a) extracting Crataegus species leaves and flowers with 45 weight percent ethanol at 60° C.; (b) separating by liquid—liquid distribution with butanol/water; and (c) isolating the composition from the water fractions.

3. A composition obtained from Crataegus species flowers and leaves prepared by a process comprising (a) extracting Crataegus species leaves and flowers with 45 weight percent ethanol at 60° C. and (b) removing flavonoids and proanthocyanidins via gel filtration of the resulting extract to yield the composition.

4. A composition obtained from Crataegus species flowers and leaves prepared by a process comprising (a) extracting Crataegus species leaves and flowers with 45 weight percent ethanol at 60° C.; (b) adsorbing the flavonoids and procyanidins in the resulting extract onto an adsorbent capable of binding the flavonoid and procyanidin components to yield a filtrate; and (c) isolating the composition from the filtrate.

5. A pharmaceutical composition comprising an effective amount of the composition of claim 1.

6. A pharmaceutical composition comprising an effective amount of the composition of claim 2.

7. A pharmaceutical composition comprising an effective amount of the composition of claim 3.

8. A pharmaceutical composition comprising an effective amount of the composition of claim 4.

9. A composition consisting of components of Crataegus species flowers and leaves where the components have a molecular weight of at least about 3000.

10. A composition according to claim 9, wherein the Crataegus species is selected from the group consisting of *Crataegus monogyna, Crataegus laevigata, Crataegus oxyacantha, Crataegus azarolus, Crataegus nigra,* and *Crataegus pentagyna.*

11. A method for treating cardiac ischemia and reperfusion-caused cardiovascular lesions comprising administering to a subject in need of such treatment an effective amount of an ethanol extract of Crataegus species flowers and leaves, the extract consisting of components having a molecular weight of at least about 3000.

12. An method according to claim 11, wherein the Crataegus species is selected from the group consisting of *Crataegus monogyna, Crataegus laevigata, Crataegus oxyacantha, Crataegus azarolus, Crataegus nigra,* and *Crataegus pentagyna.*

13. A method for treating cardiac ischemia and reperfusion-caused cardiovascular lesions comprising administering to a subject in need of such treatment and effective amount of an extract obtainable by (a) extraction of leaves and flowers of crataegus species with 45 weight percent ethanol at 60° C.; and (b) ultrafiltering the resulting extract through a membrane filter with a cut-off limit of 3000 Dalton to yield an ultrafiltered extract consisting of components having a molecular weight of at least about 3000.

14. A method for treating cardiac ischemia and reperfusion-caused cardiovascular lesions comprising administering to a subject in need of such treatment and effective amount of an extract obtainable by (a) extraction of leaves and flowers of crataegus species with 45 weight percent ethanol at 60° C.; and (b) removing flavonoids and proanthocyanidins via gel filtration of the resulting extract to yield the product.

* * * * *